United States Patent
Maier

(10) Patent No.: US 9,314,441 B2
(45) Date of Patent: Apr. 19, 2016

(54) TWO PHASE PHARMACEUTICAL DELIVERY SYSTEM

(71) Applicant: R.P. Scherer Technologies, LLC, Las Vegas, NV (US)

(72) Inventor: Hans Jürgen Maier, Schorndorf (DE)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 0 days.

(21) Appl. No.: 13/647,816

(22) Filed: Oct. 9, 2012

(65) Prior Publication Data

US 2013/0098797 A1    Apr. 25, 2013

Related U.S. Application Data

(60) Provisional application No. 61/548,837, filed on Oct. 19, 2011.

(51) Int. Cl.
| | |
|---|---|
| A61P 29/00 | (2006.01) |
| A61K 31/196 | (2006.01) |
| B65D 85/84 | (2006.01) |
| A61K 9/14 | (2006.01) |
| A61K 9/06 | (2006.01) |
| A61K 9/50 | (2006.01) |

(52) U.S. Cl.
CPC ............... *A61K 31/196* (2013.01); *A61K 9/06* (2013.01); *A61K 9/5026* (2013.01)

(58) Field of Classification Search
CPC ..... A61K 9/06; A61K 31/196; A61K 9/5026; A61K 9/5005
See application file for complete search history.

(56) References Cited

U.S. PATENT DOCUMENTS

| | | | |
|---|---|---|---|
| 3,419,657 A | 12/1968 | Sanders et al. | |
| 4,837,255 A | 6/1989 | Dechow | |
| 5,030,454 A * | 7/1991 | Theeuwes | 424/455 |
| 5,364,634 A | 11/1994 | Lew | |
| 5,858,413 A | 1/1999 | Jettka et al. | |
| 5,876,744 A * | 3/1999 | Della Valle et al. | 424/434 |
| 6,102,254 A | 8/2000 | Ross | |
| 6,399,079 B1 | 6/2002 | Mehta et al. | |
| 6,964,772 B1 | 11/2005 | Chornet et al. | |
| 2004/0109894 A1 | 6/2004 | Shefer et al. | |
| 2004/0265359 A1 | 12/2004 | Sacks et al. | |
| 2006/0177414 A1 | 8/2006 | Mertin et al. | |
| 2008/0160087 A1 | 7/2008 | Ishibashi et al. | |
| 2008/0171110 A1 * | 7/2008 | Stuart | 426/82 |
| 2008/0226705 A1 | 9/2008 | Soltero et al. | |
| 2008/0268063 A1 | 10/2008 | Jon et al. | |
| 2008/0299199 A1 * | 12/2008 | Bar-Shalom et al. | 424/484 |
| 2008/0299211 A1 | 12/2008 | Chrzan et al. | |

FOREIGN PATENT DOCUMENTS

| | | |
|---|---|---|
| EP | 1946652 A1 | 7/2008 |
| WO | WO9962498 A1 | 12/1999 |
| WO | WO0113897 A1 | 3/2001 |
| WO | WO0115750 A1 | 3/2001 |
| WO | WO2005107713 A2 | 11/2005 |

OTHER PUBLICATIONS

Schantz, Edward J., and Max A. Lauffer. "Diffusion measurements in agar gel." Biochemistry 1.4 (1962): 658-663.*
Gupta, P., et al., "Hydrogels: from controlled release to pH-responsive drug delivery," Drug Discovery Today, May 15, 2002, vol. 7, No. 10, pp. 569-579.
Peppas, N., et al., "Hydrogels for oral delivery of therapeutic proteins" Expert Opinion on Biological Therapy, Jun. 2004, vol. 4, No. 6, 881-887.
Chinese Office Action; Mailed May 6, 2015 for the corresponding CN Application No. CN201280051084.0 along with an English abstract.
European Search Report; Mailed Mar. 12, 2015 for the corresponding EP Application No. 12842547.7.

* cited by examiner

*Primary Examiner* — Abigail Fisher
*Assistant Examiner* — Daniel Branson
(74) *Attorney, Agent, or Firm* — Mendelsohn Dunleavy, PC

(57) ABSTRACT

A bi-phasic pharmaceutical composition for oral administration including one or more solid active ingredient containing particles dispersed within a semi-solid carrier formulation. The solid particles include a coating with pH-triggered drug release properties and the semi-solid carrier formulation is formulated at a pH that is different than the pH at which the active ingredient release properties of the coating are triggered. Also described is a delivery system for delivery of the bi-phasic pharmaceutical composition including the bi-phasic pharmaceutical composition described above and a dispenser pouch formed from flexible laminate sheets. Further, a process for manufacturing the two-phase pharmaceutical delivery system is described including the filling the bi-phasic pharmaceutical composition into flexible dispenser pouches, which allows the patient to squeeze and dispense the contents of the package directly into the oral cavity.

18 Claims, 1 Drawing Sheet

TWO PHASE PHARMACEUTICAL DELIVERY SYSTEM

BACKGROUND OF THE INVENTION

1. Field of Invention

The present invention relates to pharmaceutical delivery systems and, more particularly, to pharmaceutical delivery systems in the form of a dispersion of particles in a gel.

2. Brief Description of the Prior Art

Solid oral pharmaceutical dosages are typically administered in the form of pills, granules, powders, and strips. However, some patients, particularly pediatric and geriatric patients, have difficulty swallowing or chewing many types of conventional solid dosage forms.

One option is the use of soft capsule dosage forms containing a liquid fill material. In capsule fill compositions which can be used in soft capsules, the active ingredient must be solubilized in a solvent. Also, the fill composition must be chemically compatible with the capsule material, as well as being inert relative to the active ingredient. Further, the biological activity of the active ingredient must be preserved in the formulation. As a result, there are significant developmental challenges for developing suitable soft capsule dosage forms.

Another option is to formulate semi-solid pharmaceutical formulations. One example of such a formulation is described in WO 99/62498 which employs a water soluble gel containing an active agent. The formulations are sufficiently viscous to be spill resistant but can still be squeezed from a tube. Another example of such a semi-solid pharmaceutical formulation is described in U.S. Pat. No. 6,102,254.

Another problem that needs to be addressed is the potentially unpleasant taste of many drugs. As a result, there is often a need for taste-masking of such drugs to ensure patient compliance. The challenge of a new form of drug administration is to improve patient compliance and to enhance the therapeutic effects of oral pharmaceuticals.

Hence there is a need for a delivery system that exhibits properties that will enhance patient compliance, offer enhanced therapeutic effects, and potentially provide additional enjoyment above and beyond health benefits.

SUMMARY OF THE INVENTION

The present invention is directed to a bi-phasic pharmaceutical composition for oral administration, comprising one or more solid active ingredient containing particles dispersed within a semi-solid hydrogel carrier formulation. The solid particles include a coating with pH-triggered drug release properties and the semi-solid carrier formulation is formulated at a pH that is different than the pH at which the active ingredient release properties of the coating are triggered.

The present invention is also directed to a delivery system for delivery of a bi-phasic pharmaceutical composition. The delivery system includes the bi-phasic pharmaceutical composition described above and a dispenser pouch formed from flexible laminate sheets.

In another aspect, the present invention relates to a process for manufacturing the delivery system of the invention. The process includes a step of filling the bi-phasic pharmaceutical composition into flexible dispenser pouches, which allows the patient to squeeze and dispense the contents of the package directly into the oral cavity.

The present invention thus provides a new way to deliver of oral pharmaceutical compositions that will improve patient compliance.

DETAILED DESCRIPTION OF THE PREFERRED EMBODIMENTS

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

It must be noted that as used herein and in the appended claims, the singular forms "a", "an", and "the" include plural references unless the context clearly dictates otherwise. As well, the terms "a" (or "an"), "one or more" and "at least one" can be used interchangeably herein. It is also to be noted that the terms "comprising", "including", and "having" can be used interchangeably.

The term "oral delivery" as used herein means ingestion through the mouth by swallowing.

The term "two-phase or bi-phasic pharmaceutical composition" as used herein means a heterogenic macroscopic system consisting of a solid phase and a semi-solid phase.

The term "semi-solid" as used herein means a physical state that shares some properties of liquids such as shape conformity to something applying pressure to it, or the ability to flow under pressure while also sharing some similarities to a solid in that it can support its own weight and hold its shape.

The present invention provides a two-phase pharmaceutical composition including a semi-solid phase and a solid phase dispersed in the semi-solid phase. The solid phase includes one or more pharmaceutical substances. The invention allows the production of tailored doses and strengths for the pharmaceutical compositions by providing the ability to significantly vary the amount of active ingredient in the composition while still preserving a pleasant taste perception and without rendering the composition difficult to ingest.

Figure 1:
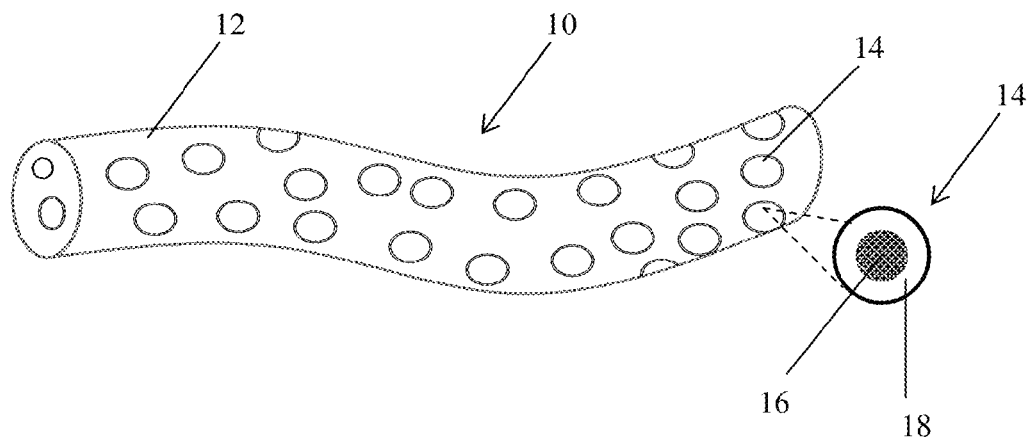
FIG. 1 depicts one example of a bi-phasic pharmaceutical composition in accordance with the present invention.

An exemplary two-phase ("bi-phasic") pharmaceutical composition 10 is depicted in FIG. 1. The pharmaceutical composition 10 includes a semi-solid carrier material 12 having dispersed therein a plurality of solid particles 14. The solid particles 14 contain at least an active ingredient 16 and a coating 18 located on active ingredient 16.

It is possible to vary the size and/or amount of the solid particles 14 in the semi-solid carrier 16 in order to vary the amount of active ingredient 16 in the pharmaceutical composition 10. In this manner, the dosage delivered by a particular pharmaceutical composition can be easily tailored to a desired level.

In one aspect, the invention provides one or more solid active ingredients for oral administration. The active ingredients may, for example, include pharmaceutical agents such as prescription drugs, over-the-counter drugs or experimental drugs, nutraceuticals and nutritional supplements and other health supplements that are suitable for oral administration. Subjects or patients may, for example, include pediatric, adult and/or geriatric subjects. The solid active substance will generally include an active agent that falls into the ATC classification system (Anatomical Therapeutic Chemical Classification System).

The active ingredient is coated to form particles and provide a physical barrier between the active ingredient and the semi-solid carrier. By use of such a barrier, the solubility of the solid active ingredient containing particles in water and water-containing systems can be controlled. Preferred solid particles containing active ingredients are slightly soluble or practically insoluble in water to prevent dissolution of the active ingredient in the semi-solid carrier.

At least one coating on the solid particles containing the active ingredient is designed to disintegrate or dissolve at a certain pH or within a certain pH range. The disintegration or dissolution of the coating is triggered by a certain pH of the environment to which the coating is exposed. Such coatings are referred to as "pH-triggered coatings." Each coating will thus have a particular pH or range of pH at which disintegration or dissolution of the coating is triggered. The pH-triggered coating may be the only coating on the active ingredient or it may be added in addition to one or more other coatings in order to form the solid particles. If the pH-triggered coating is the only coating on the active ingredient it can function as both the physical barrier coating, as necessary, and the pH-dependent coating that is triggered to disintegrate or dissolve at a particular pH or within a particular pH range.

In certain embodiments, active ingredients are coated with functionalized polymers with pH-triggered drug release properties resulting from ionization of the polymer. Active ingredients coated with such coating systems release the coated material dependent upon the pH that initiates breakdown of the coating material, as characterized by the pKa or pKb values of the polymers. pH sensitive polymers contain a certain degree of acidic or basic functional groups fixed on the polymer backbone. The functional groups either accept or release protons in response to appropriate pH and ionic strength changes in aqueous media. The network porosity of the polymer coatings changes due to electrostatic repulsion.

Ionic polymer coatings containing carboxylic acid, sulfonic acid or other acidic groups show changes in their dynamic and equilibrium swelling behavior, network structure, permeability and mechanical strength as a result of pH variations. As a result, disintegration of coatings containing such materials can be influenced by changing the external pH to which the coating is exposed. Conversely, coating polymers containing basic pendant groups, such as amines, ionize and show electrostatic repulsion at low pH and thus can be triggered at a different pH than polymers containing acidic pendant groups.

pH-dependent coating polymers are a subclass of pH-triggered coatings and may be grouped into two main classes: cationic polymers and anionic polymers. Cationic coatings swell and release the active ingredient in a low pH environment, e.g. in the stomach, whereas anionic coatings swell and release actives in a neutral environment. pH-dependent coatings and methods for applying pH dependent coatings are known in the art.

Particular examples of pH dependent coatings include polymers of compounds such as, for example cellulose acetate phthalate, cellulose acetate trimelliate; hydroxypropyl methylcellulose phthalate; hydroxypropyl methylcellulose acetate succinate; polyvinyl acetate phthalate; acrylic and methacrylic acid polymers and copolymers containing carboxylic acid functional groups, and aminoalkyl methacrylic acid polymers containing functional groups such as dimethyl aminoethyl, and trimethylammonioethyl, and the like.

Non-ionic materials such as, lipids, waxes, fats and fatty acids, mono-, di- and triglycerides, e.g. distearate, dibehenate, trilaurin, triolein, and trimyristate, and acetylated mono- and diglycerides, beeswax, and carnauba wax may also be employed for the coating. Lipophilic coating materials provide excellent resistance of the active ingredient-loaded particles against the semi-solid hydrogelic matrix.

Suitable coating materials may further comprise pH and rheological modifiers, solvents, cross-linking agents, glidants and anti-tackifying agents, pigments, dyes, emulsifiers, stabilizers, flavours and sweeteners, and permeability enhancers.

The coating can be applied by use of well known coating techniques such as conventional pan or fluid bed coating, compression coating, hot-melt coating, photocurable coating, supercritical fluid coating, dry powder coating, electrostatic coating, and solvent and solvent-free hot and cold extrusion techniques. Fluid bed coating is particularly preferred for smaller particles and pellets.

When pH is to be used as a trigger, the semi-solid carrier will have a pH different from the pH trigger point of the coating polymer, to ensure that the specific dissolution pH, rather than the semi-solid carrier, initiates active substance release. Preferably, the pH of the semi-solid carrier will differ by at least 2.0 from the pH at which the pH-dependent coating is triggered, and, more preferably, by at least 3.0 from the pH at which the pH-dependent coating is triggered to disintegrate or dissolve.

In some embodiments the coated active ingredients may be shaped in a conventional industrial process to provide known solid forms such as active ingredient loaded granulates, mini-tabs, extrudates, pellets, beads, and prills. The solid forms may be provided in any technically feasible shape, with the preferred shape being spherical or substantially spherical particles, as well as regular or irregular ovaloid shaped particles. The size of individual particles, or the largest dimension in the case of irregular shaped particles, may range from 1 µm-1,000 µm, preferred are 10 µm-750 µm, more preferred are particles having a size or largest dimension of 50 µm-500 µm. The quantity of the active ingredient in the solid particles is determined by the dosage required for a particular therapeutic use. The solid particles may comprise additional components such as, for example, builders, binders, disintegrants, and glidants.

In a further principal aspect, the invention provides a gel composition as a semi-solid carrier. The semi-solid carrier has dispersed therein multiple particulate solid particles comprising a coated active ingredient, as described above. The coated solid particles are designed to be slightly or practically insoluble in the semi-solid carrier material to form a biphasic system.

The gel is preferably a viscoelastic gel which may be characterized as a hydrogel in that the semi-solid carrier will contain at least 20% of the total weight of water. The carrier material is a semi-solid material which is characterized by rheological properties which resemble, in part, the rheological behaviour of a viscous fluid and, also in part, that of an elastic solid. The semi-solid carrier behaves like a solid upon the exertion of low shear force, and like a viscous fluid when the shear force exceeds a threshold that is termed the yield point. The carrier material of the invention is a system with a finite, rather low, yield stress.

A hydrogel composition is defined by the presence of at least 20% of the total weight of water, relative to the total mass of the composition. In a typical hydrogel, the water forms a continuous phase in which the solid components which impart the gel strength to the system are dispersed. Among the hydrophilic polymers which are suitable for carrying out the present invention are, for example, hydrophilic polysaccharides, including native and derivatized polysaccharides, such as dextran, starch, amylose, amylopectin, cellulose, alginic acid, pectin, chitosan, hyaluronic acid, xanthan gum, pullulan, gellan gum, agar, carrageenan, dextrin, guar gum, carob gum, and inulin, and hydrophilic proteins, polypeptides, including albumin, lysozyme, synthetic poly (amino acids), gelatine A, gelatine B; collagen, poly(lysine) and related copolymers, poly(glutamic acid) and related copolymers, elastin, fibrin, casein, whey protein, lactoglobulin, lactalbumin, and soy protein, and synthetic hydrophilic polymers such as poly(acrylates), poly(acrylamides), poly (alkyl acrylates), poly(alkyl acrylamides), in particular poly (methacrylate), poly(hydroxyethyl methacrylate), poly(hydroxypropyl methacrylate), poly(hydroxyethyl methacrylamide), poly(hydroxypropyl methacrylamide); polyvinyl alcohol, poly(ethylene glycol), water soluble polyphosphazenes, and mixtures of any one or more of the above.

Other ingredients such as solvents, wetting agents, rheological modifiers, pH-modifiers, cross-linking agents, preservatives, sweeteners, flavoring agents, and surfactants, as well as other excipients known to a person skilled in the art can also be included in the semi-solid carrier material.

In one aspect of the invention, the texture of the semi-solid carrier is such that it will be perceived as pleasant. Besides the chemical nature of the polymeric matrix and the solvent—usually water—the most influential parameters for a desired texture are the molecular weight and molecular weight distribution, the degree of branching, the degree of crystallinity and the concentration of the gel forming polymer in the solution, as well as the amount of water, diluents and rheological modifiers. The water content of preferred hydrogels is typically ranging between 20 and 90% w/w; more preferably 25-80% w/w and most preferably 30-70% w/w, based on the total weight of the hydrogel.

The texture and the mechanical performance of materials that are intermediate between liquids and solids can be described by a substance's tendency to be deformed when a force is applied to it. The viscoelastic property of the polymer can be characterized by dynamic mechanical analysis (DMA) where a force (stress) is applied to a material and the resulting displacement (strain) is measured. For a perfectly elastic solid, the resulting strain and the stress will be perfectly in phase. For a purely viscous fluid, there will be a 90 degree phase lag of strain with respect to stress. The strain of a viscoelastic body is out of phase with the stress applied due to the excess time necessary for molecular motion and relaxation to occur. The ratio of the elastic stress to strain is the elastic (or storage) modulus E'; the ratio of the viscous stress to strain is the viscous (or loss) modulus E" when testing is done in tension or flexure rather then in shear. The storage modulus is related to stiffness, and the loss modulus to damping and energy dissipation.

The elastic modulus E' of a gel increases with the increase of the dry polymer concentration as a portion of the hydrogel. In preferred embodiments E' is in the range of 0.05 kPa to 500 kPa at 20° C. within the linear viscoelastic region, more preferred is a gel with E' the range of 0.5 kPa-50 kPa. In preferred embodiments the ratio of the elastic modulus to the viscous modulus is 1:2.5-2.5:1; and more preferred are ratios of the elastic modulus to the viscous modulus of between 1:1.5 and 1.5:1.

The elastic modulus of a hydrogel can be tuned using diluents such as, for example, water, glycerol, glycols such as ethylene glycols and propylene glycols or polymers thereof, polyvinyl alcohols, polyvinyl acetate, polyethylene oxides, anionic, cationic or neutral tensides such as sorbitan esters (spans), ethoxylated sorbitan fatty esters, (polysorbate), glycerol esters, polyglycerol esters, fatty alcohol ethoxylates, fully or partially hydrated starch degradation products such as sorbitol, maltitol, maltitriol, xylitol, erythritol, arabitol, adonitol, mannitol, iditol, galactitol, and allitol, and esters of organic acids such as formic acid, lactic acid, citric acid, tartaric acid, and fumaric acid as well as mixtures thereof.

Excipients or other agents that may enhance the physical properties of the semi-solid carrier material to support swallowing or preserve the activity of the active ingredient loaded solid particles may be included alone or in combination. Examples of excipients include olfactory stimulants, salivation stimulants, pH modification agents, sweeteners, flavouring agents, taste masking agents, antioxidants, natural or artificial flavours, surfactants, colorants, natural or synthetic plant extracts and humectants.

In preferred embodiments, decomposition of the hydrogel is prevented by employing preservatives such as antioxidants (e.g. BHA; BHT), calcium proprionate, sodium proprionate, sodium nitrate, sodium nitride, sulfites and disodium EDTA.

The pH of the semi-solid carrier should be substantially different than the pH required to trigger disintegration or dissolution of the coating of the solid active ingredient containing particle. The pH of the semi-solid carrier can be adjusted relative to the pH of the solid active ingredient containing material by use of suitable acids or bases. Suitable acids comprise pharmacopoeial weak inorganic and organic acids having a pKa value >2, and more preferable is a pKa of 3-6. Such acids include, for example, carbonic acid, hydrogen phosphoric acids, and mono and polybasic organic acids such as lactic acid, acetic acid, formic acid, citric acid, oxalic acid, tartaric acid, and amino acids. Preferred bases are pharmacopoeial alkali metal, alkaline earth metal or ammonium salts of the above-mentioned weak acids. Most preferred are mixtures of a weak acid and its conjugated base component to form a buffer system. Buffer systems are used as a means of maintaining the pH at a nearly constant value. Preferred buffer systems are, for example, hydrochloric acid/citric acid for a pH of 1-5; citric acid/sodium citrate for a pH of 2.5-5.5; acetic acid/sodium acetate for a pH of 3.5-5.5; and potassium hydrogen phosphate buffers for a pH of 5.8-8.

Preferred hydrogel semi-solid carrier compositions contain sweeteners. The term "sweetener" as used herein means natural sweeteners such as sugars, e.g. glucose, fructose, saccharose, agarose, and/or artificial sweeteners such as, for example, stevia, aspartame, sucralose, neotame acesulfame potassium and saccharin. Preferred is a sweetener content of 1-40% w/w related to the total weight of the semi-solid carrier material.

Preferred embodiments contain flavouring agents or aromas. Suitable flavouring agents include anise, oil of peppermint, oil of clove, eucalyptus, lemon, lime, honey lemon, red fruit, grapefruit, orange and, cherry oils and essences as well as cooling agents and warming agents such as carboxamides, menthols, thymol, camphor, capsicum, phenol, eucalyptus oil, benzyl alcohol, salicyl alcohol, ethanol, clove bud oil, hexylresorcinol, ketals, diols, and mixtures thereof. Most preferred is vanillin. Preferred embodiments contain one or more taste masking agents used for masking of unpleasant tastes in the end products. One example of a suitable taste-masking agent is "Mask-it" from Firmenich.

Preferred hydrogel compositions contain a pharmaceutically active ingredient designed for buccal/immediate release, which is dissolved in the hydrogel. The active ingredient in the hydrogel may be the same or different from the active ingredient contained in the coated solid material. The combination of an active ingredient for immediate release dissolved in the hydrogel and an active ingredient with delayed or sustained release contained in the solid material may provide therapeutic benefits. Preferred hydrogel compositions may contain absorption enhancers to facilitate or accelerate buccal release.

Figure 2:
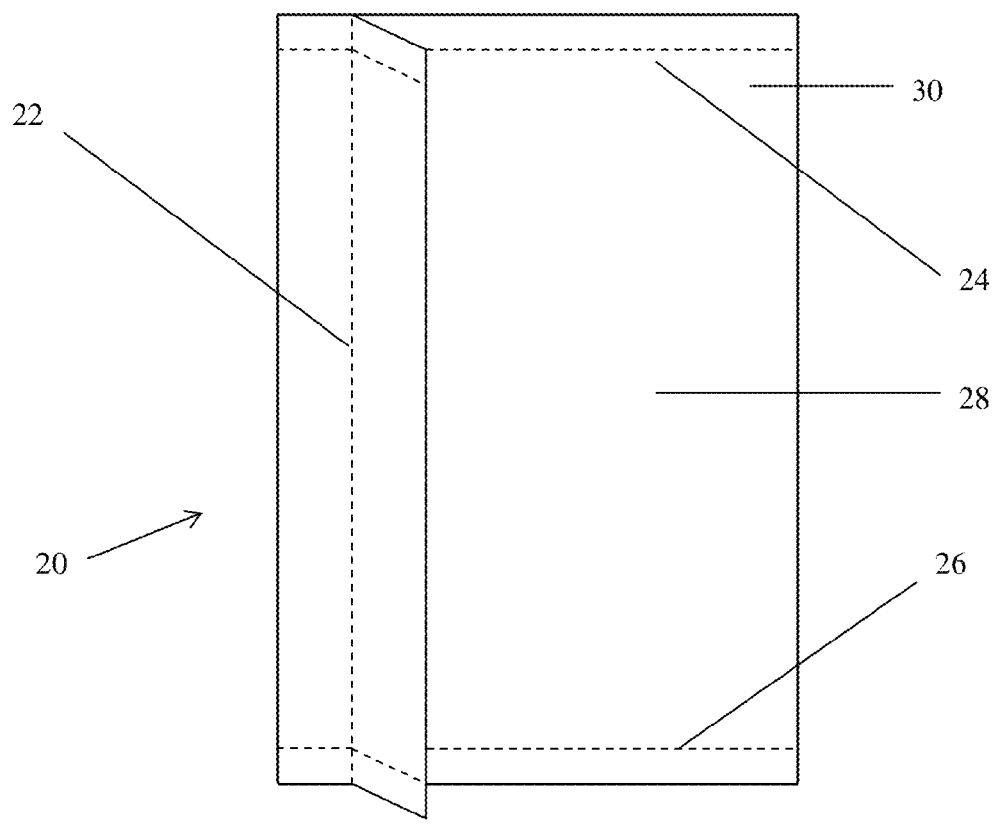
FIG. 2 depicts a dispenser pouch for a delivery system for the bi-phasic pharmaceutical composition of the present invention.

In a further aspect the invention relates to a dispenser pouch 20, shown in FIG. 2. The dispenser pouch 20 may be formed of flexible sheets joined along the edges thereof by horizontal seams 24, 26 to define a storage compartment 28 suitable for holding at least one dose of a pharmaceutical composition, especially a flavoured product. The dispenser pouch 20 may be a three seal sachet, or stick pack, made from a flexible laminate sheet, having a fin seal 22 along a longitudinal axis and transverse fin seals 24, 26 at each end. The laminate sheet is tough enough to resist tearing unless a notch is provided with which to initiate a tear. The dispenser pouch 20 includes a portion 30 designed such that part of the storage section 28 can be cut off the remaining portion of the storage section 28 when the pouch 20 is opened, thereby defining a discharge opening. For dispensing semi-solid materials through the discharge opening pressure must be applied in order to initiate product flow.

Preferred dimensions of a sachet used as dispenser pouch 20 are a length of from about 2 cm to about 10 cm along its longitudinal edges and a width of from about 10 mm to about 35 mm along its transverse seals. The sachet will generally contain from 0.5 to about 10 g of product. The pharmaceutical product for which the sachet is intended is preferably a semi-solid material.

The materials used to construct the laminate sheet can be any that suitable, conventional materials such as polyester, polypropylene, polyethylene and polyethylene terephthalate (PET). The sachet should be sufficiently tear resistant to substantially prevent tearing until the sachet is correctly manipulated to open the package. In preferred embodiments the laminate comprises a layer of aluminium foil which forms a pharmaceutical composition contacting surface on the inside of storage section 28.

In another aspect, the present invention relates to a process for manufacturing the pharmaceutical delivery system of the invention. The process includes the steps of formulating the bi-phasic pharmaceutical composition and filling the bi-phasic pharmaceutical composition into flexible dispenser pouches, which allow the patient to squeeze and dispense the contents of the package directly into the oral cavity. Due to the semi-solid nature of the product of the invention, the patient can ingest the composition without the need to drink since the composition is not in a liquid form or chew the composition due to the gelatinous nature of the hydrogel and the small size of the solid particles contained therein.

The invention is useful when the active ingredient is a bitter tasting agent since the active ingredient is coated with a coating that forms a barrier between the active ingredient and the hydrogel to control the solubility of the active ingredient in the hydrogel. Thus, the active ingredient is maintained in the hydrogel until exposed to a pH which triggers disintegration or dissolution. As a result, the patient need not taste the bitter taste of the active ingredient and only experience the pleasant tasting hydrogel which may include flavours and/or taste-masking agents.

The invention is also useful when the active ingredient is intended for administration to pediatric and geriatric patients since the semi-solid form of the product makes it easier to swallow than many conventional delivery systems such as tablets, capsules, pills, etc.

The invention is particularly useful when the active ingredient is acid sensitive, e.g. when gastro-resistant properties are required for delivery of the active ingredient to, for example, the lower intestine for absorption into the body. The combination of the coating on the particles and the hydrogel can be used not only to control solubility and trigger disintegration or dissolution of the particles by exposure to a particular pH, but also to render the particles resistant to the gastro-intestinal system. This can be accomplished, for example, by use of an enteric coating which does not disintegrate or dissolve at a pH of about 5 or less, as would typically be encountered in the stomach, but will dissolve at a pH of about 7-9 as may be encountered in the intestinal tract.

The invention is also useful when large amounts of active ingredient are beneficial or required to achieve the desired therapeutic effect. This is because, due to the nature of the delivery system, the amount of active ingredient contained in a particular dose is not constrained by a size of a tablet, capsule or pill. In other words, the fact that a larger amount of the pharmaceutical composition of the present invention needs to be administered only requires the patient to swallow more of the semi-solid material rather than requiring the patient to swallow, for example, a very large pill. As a result, even for large dosages of active ingredient, ingestion of the pharmaceutical composition will not be difficult or unpleasant for the patient.

The invention is especially useful when different modes of action should be administered in one dose, e.g. immediate and delayed release or synergistic combinations of active ingredients. More specifically, to achieve immediate release, one or more active ingredients can be included in the semi-solid hydrogel component of the pharmaceutical composition in addition to inclusion of one or more active ingredients in the solid particle component of the pharmaceutical composition. In this manner, immediate release of the active in the hydrogel component can be achieved, while preserving delayed release of the active in the solid particle as a result of the pH-triggered dissolution of the coating on the solid particle.

The invention is also particularly useful when different modes of oral administration are beneficial or required, e.g. a combination of buccal and gastric absorption. This combination can be achieved by the provision of an active ingredient in the semi-solid hydrogel component of the pharmaceutical composition which is suitable for buccal administration since this active ingredient will be bioavailable when the pharmaceutical composition is located in the oral cavity. The solid particle component of the pharmaceutical composition can be designed not to disintegrate or dissolve under the conditions encountered in the oral cavity but instead to dissolve or disintegrate in the gastrointestinal tract instead. In this manner, a combination of different modes of administration can be achieved using the same pharmaceutical composition.

EXAMPLES

Typically, a hydratable polymeric material such as, but not limited to gelatine, is mixed with water and excipients and other additives in suitable ratios to form an aqueous suspension. The aqueous suspension is then processed to induce formation of a liquid sol by heating. The solid particles loaded with active ingredient are dispersed into the liquid sol at appropriate levels and then the biphasic mixture is filled into single dose delivery devices such as stick packs. The suspension is then processed to induce gelling by cooling.

Example 1

To prepare a citrate buffer, 38.43 g of citric acid was dissolved in 2000 ml water to make solution A; 17.80 g of disodium hydrogen phosphate dehydrate was dissolved in 500 ml water to make solution B. Citrate buffer C of pH 2.5 was prepared by mixing 2000 ml of solution A with 85 g of solution B.

To prepare gelatine hydrogel D, 100.00 g gelatine (Gelita; bovine gelatine 230 bloom) was dispersed in 900.00 g of cold citrate buffer from Example C. The gelatine was soaked overnight at 25° C. The suspension was then heated to 65° C. and homogenized. The gel was cooled to 45-60° C. The pH of the gel was adjusted by adding about 40.0 g of anhydrous citric acid until reaching a pH of 2.5 to make hydrogel D.

850.0 g of diclofenac sodium pellets was coated in an ALLGAIER Fluid Bed Coater with 1000.0 g of a functional polymer (Eudragit® FS 30D, pKa about 6.8), plus 250 g of water. The process temperatures were as follows: inlet air temperature: 43-46° C.; outlet air temperature: 24-26° C.; core temperature: 25-27° C. The spray rate was 5-7 g/minute. The spraying time was about 150 minutes. The procedure resulted in diclofenac sodium pellets E with an API content of 53.2% w/w. 3 g of warm gelatine hydrogel from Example D was poured into snap on lid vials.

The vials were cooled until the hydrogel was settled. 190 mg coated diclofenac sodium pellets from Example E was dispersed in the settled gelatine mass before layering with an additional 2 g of warm gelatine hydrogel from Example D. The closed vials were shaken vigorously for the purpose of homogeneously dispersing the diclofenac pellets in the molten gelatine mass. A total of 100 vials of active samples were made and stored at 25° C. with 60% relative humidity and also at 40° C. and 75% relative humidity.

After one month of storage, no diclofenac sodium was detected in the gelatine mass by the HPLC UV method in the samples stored at 25° C./60% RH and the samples stored at 40° C./75% RH % (assay diclofenac Na in gelatine in all tested samples <0.1% w/w). This indicated that the coated API loaded pellets were stable in the pH-adjusted matrix for at least one month. Further, the microbiological quality was tested after a one month storage period according to Ph.Eur.5.1.4. and microbial purity was demonstrated (TAMC<10 cfu; TYMC<10 cfu; $E.\ coli$ not detected).

After three months storage, the stability of the coated API loaded pellets stored at 25° C./60% RH and 40° C./75% RH was tested again and no significant amounts of diclofenac sodium were detected in the gelatinous matrix (assay diclofenac Na in gelatine <0.1% w/w). No relevant growth of bacteria or funghi could be detected (TAMC<10 cfu; TYMC<10 cfu; $E.\ coli$ not detected).

Analytical Methods

The following analytical procedures were employed:
Chromatographic Method

| | |
|---|---|
| HPLC column: | Inertsil ODS-3, 3 μm column (50 × 4.6 mm);. |
| mobile phase: | aqueous 0.05M $KH_2PO_4$-of pH 3.8 + acetonitrile 40 + 60 (v, v) |
| injection volume: | 10 μL |
| wavelength: | 276 nm |
| flow rate: | 1.5 mL/min |

Sample Preparation

The sample was in a water bath to 50-60° C. until the sol state of the matrix was achieved. The liquid fraction of the sample was transferred into a 100 mL volumetric flask, taking care that no diclofenac sodium pellets were transferred. The pellets were treated using a few ml of water for 30 seconds and the aqueous phase was transferred into the volumetric flask. The rinsing procedure was repeated until the matrix was completely transferred. The combined sample was treated for 10 minutes in an ultrasonic bath, then filled to volume and mixed well.

Test procedure

Perform the system suitability test as required for instrument qualification.

Perform the test on the sample.

Microbiological purity testing Follow the requirement as mentioned in Ph.Eur. 5.1.4 "Microbiological quality of non-sterile pharmaceutical preparations and substances for pharmaceutical use".

| Microbial purity | Specification |
|---|---|
| Total aerobic microbial count (TAMC) | ≤$10^3$ cfu/g |
| Total yeasts and moulds count (TYMC) | ≤$10^2$ cfu/g |
| $Escherichia\ coli$ | absent in 1 g |

Example 2

A gelatinous hydrogel F with a viscosity higher than the hydrogel of Example 1 was prepared by dispersing 300.00 g gelatine (Gelita, bovine gelatine 230 bloom) in 700.00 g of cold citrate buffer C from Example 1. The gelatine was soaked overnight at 25° C. The suspension was then heated to 65° C. and homogenized. The gel was cooled to 45-60° C. The pH of the gel was adjusted by adding about 30.0 g of anhydrous citric acid until reaching a pH of 2.5.

Samples were prepared by dispersing 5 g pellets taken from approach E of Example 1 into the hydrogel F using the same procedure as described in Example 1. A total of 100 vials of active samples were made and stored at 25° C. with 60% relative humidity and also at 40° C. and 75% relative humidity.

The stability data taken after one and three months storage were largely identical to those of Example 1 and demonstrated the excellent chemical and microbiological stability of the coated API loaded pellets in the pH-adjusted hydrogel matrix. Sssays of diclofenac Na in gelatine of 0.1% w/w were taken and no relevant growth of bacteria and funghi were detected using a threshold of TAMC<10 cfu; TYMC<10 cfu, and $E.\ coli$ not detected.

Example 3

25 g of gelatine (Gelita, bovine gelatine, 160 bloom) was dispersed in 150 ml cold citrate buffer C from Example 1. The gelatine was soaked overnight at 25° C. before the suspension was heated to 50-60° C. for 10 minutes with vigorous stiffing. 1.9 g of sodium citrate was added to adjust the pH to 3. 25 g enterically coated diclofenac pellets E were added and homogeneously dispersed in the warm suspension. The mixture was then filled in portions of 3 g into stick packs to obtain a two-phase delivery system containing 100 mg diclofenac per dose. The single dose form allowed dispensing of the diclofenac directly into the mouth. The system promoted excellent compliance and good palatability with acceptable taste The foregoing examples have been presented for the purpose of illustration and description and are not to be construed as limiting the scope of the invention in any way. The scope of the invention is to be determined from the claims appended hereto.

What is claimed is:

1. A pharmaceutical composition for oral administration comprising:
    a semi-solid hydrogel having a water content of at least 20% by weight, based on the total weight of the hydrogel, said hydrogel is a viscoelastic gel having an elastic modulus which is measured at 20° C. of 0.05 kPa to 500 kPa and which is prepared by heating an aqueous suspension of a hydratable polymeric material to induce formation of a liquid sol, followed by cooling the sol to induce gelling,
    a plurality of coated active ingredient containing particles dispersed in said hydrogel, wherein less than 0.1 wt % of the active ingredient is detectable in the hydrogel one month after the preparation of the composition,
    at least one coating of said particles is triggered to disintegrate or dissolve by exposure to a particular pH range as a result of which the active ingredient is released,
    the hydrogel having a pH sufficiently different from the pH that triggers disintegration or dissolution of the at least one coating of the particles so as to prevent the release of the active ingredient from the particles into the hydrogel,
    wherein the hydrogel comprises a buffer system, and
    the at least one coating consists of: a) an ionic polymer; or b) non-ionic material selected from the group consisting of lipids, waxes, fats, fatty acids, mono-, di- and triglycerides, acetylated mono- and diglycerides, beeswax, and carnauba wax; and optionally c) at least one selected from the group consisting of pH modifiers, rheological modifiers, solvents, cross-linking agents, glidants, anti-tackifying agents, pigments, dyes, emulsifiers, stabilizers, flavours, sweeteners, and permeability enhancers.

2. The pharmaceutical composition as claimed in claim 1, wherein the pH of the hydrogel differs from the pH that triggers disintegration or dissolution of the at least one coating of the particles by at least 2.0.

3. The pharmaceutical composition as claimed in claim 1, wherein the pH of the hydrogel differs from the pH that triggers disintegration or dissolution of the at least one coating of the particles by at least 3.0.

4. The pharmaceutical composition as claimed in claim 1, wherein the at least one coating is an ionic polymer.

5. The pharmaceutical composition as claimed in claim 4, wherein the ionic polymer is a cationic polymer.

6. The pharmaceutical composition as claimed in claim 4, wherein the ionic polymer is an anionic polymer.

7. The pharmaceutical composition as claimed in claim 6, wherein the at least one coating on said particles is an enteric coating.

8. The pharmaceutical composition as claimed in claim 1, wherein the buffer system maintains the pH of the hydrogel at a pH of about 5 or less.

9. The pharmaceutical composition as claimed in claim 1, wherein the buffer system maintains the pH of the hydrogel at a pH of about 5.5-8.

10. The pharmaceutical composition as claimed in claim 1, wherein the hydrogel has a water content of from about 25% to about 90% by weight, based on the total weight of the hydrogel composition.

11. The pharmaceutical composition as claimed in claim 1, wherein the at least one coating on said particles is insoluble or only slightly soluble in water.

12. The pharmaceutical composition as claimed in claim 1, wherein the hydrogel comprises at least one active ingredient which may be the same or different from the active ingredient of the coated particles.

13. The pharmaceutical composition as claimed in claim 1, wherein the hydrogel is a viscoelastic gel having an elastic modulus which is measured at 20° C. of 0.5 kPa to 50 kPa.

14. A delivery system for the oral administration of a biphasic pharmaceutical composition comprising:
    a pharmaceutical composition comprising:
        a semi-solid hydrogel having a water content of at least 20% by weight, based on the total weight of the hydrogel, said hydrogel is a viscoelastic gel having an elastic modulus which is measured at 20° C. of 0.05 kPa to 500 kPa and which is prepared by heating an aqueous suspension of a hydratable polymeric material to induce formation of a liquid sol, followed by cooling the sol to induce gelling, and
        a plurality of coated active ingredient containing particles dispersed in said hydrogel,
    wherein less than 0.1 wt % of the active ingredient is detectable in the hydrogel 1 month after the preparation of the composition,
    at least one coating of said particles it triggered to disintegrate or dissolve by exposure to a particular pH range as a result of which the active ingredient is released, and
    a dispenser pouch formed from flexible laminate sheets,
    the hydrogel has a pH sufficiently different from the pH that triggers disintegration or dissolution of the at least one coating of the particles so as to require exposure of the pharmaceutical composition to an external stimulus in order to trigger disintegration or dissolution of the at least one coating of said particles and release of the active ingredient,
    wherein the hydrogel comprises a buffer system, and
    the at least one coating consists of: a) an ionic polymer; or b) non-ionic material selected from the group consisting of lipids, waxes, fats, fatty acids, mono-, di- and triglycerides, acetylated mono- and diglycerides, beeswax, and carnauba wax; and optionally c) at least one selected from the group consisting of pH modifiers, rheological modifiers, solvents, cross-linking agents, glidants, anti-tackifying agents, pigments, dyes, emulsifiers, stabilizers, flavours, sweeteners, and permeability enhancers.

15. The delivery system as claimed in claim 14, wherein the pH of the hydrogel differs from the pH that triggers disintegration or dissolution of the at least one coating of the particles by at least 2.0.

16. The delivery system as claimed in claim 14, wherein the at least one coating is an ionic polymer.

17. The delivery system as claimed in claim 14, wherein the at least one coating is an enteric coating.

18. The delivery system as claimed in claim 14, wherein the dispenser pouch is a stick pack.

* * * * *